United States Patent [19]
Johnson et al.

[11] Patent Number: 5,968,514
[45] Date of Patent: Oct. 19, 1999

[54] METHODS FOR STIMULATING IMMUNE RESPONSES IN A HOST THROUGH THE ADMINISTRATION OF SUPERANTIGEN PEPTIDES DERIVED FROM HUMAN IMMUNODEFICIENCY VIRUS TYPE 1 NEF

[75] Inventors: Howard M. Johnson; Barbara A. Torres; Janet K. Yamamoto, all of Gainesville, Fla.

[73] Assignee: University of Florida, Gainesville, Fla.

[21] Appl. No.: 08/331,454

[22] Filed: Oct. 31, 1994

Related U.S. Application Data

[63] Continuation-in-part of application No. 08/145,708, Oct. 29, 1993, Pat. No. 5,519,114.
[51] Int. Cl.$^6$ .......................... A61K 39/21; A61K 38/00; C07K 1/00
[52] U.S. Cl. .................................. 424/188.1; 424/208.1; 530/300; 530/350; 435/5
[58] Field of Search .......................... 424/208.1; 435/7.1; 530/324

[56] References Cited

U.S. PATENT DOCUMENTS 5,221,610   6/1993   Montagnier et al. .................... 435/7.1

FOREIGN PATENT DOCUMENTS 2650954   4/1989   France .
8909227   10/1989   WIPO .

OTHER PUBLICATIONS

Held, B.W. et al. (1992) "An Exogenous Mouse Mammary Tumor Virus with Properties of Mls–1$^a$ (Mtv–7)" J. Exp. Med. 175:1623–1633.

Choi, T. et al. (1991) "A superantigen encoded in the open reading fram of the 3' long terminal repeat of mouse mammary tumour virus" Bature 350(6315):203–205.

Acha–Orbea H. et al. (1991) "Clonal deletion of Vβ14–bearing T cells in mice transgenic for mammary tumour virus" Nature 350(6315):207–209.

Korman, A.J. et al. (1992) "The mouse mammary tumour virus long terminal repeat encodes a type II transmembrane glycoprotein" The EMBO Journal 11(5):1901–1905.

Torres, B.A. et al. (1993) "Bacterial and Retroviral superantigens share a common region on class II MHC antigens" The Journal of Immunology, Abstracts Part II, p. 287A, abstract No. 1642.

O'Neill, H.C., C. Jolly (1992) "Retroviral superantigens" Immunology Today 13(11):462–463.

Acha–Orbea, H. (1993) "Superantigens Expressed by Mouse mammary Tumor Virus" Current Communications in Cellular and Molecular Biology 7:31–44.

Cernescu, C., S. Ruta (1992) "Biological roles of HIV Nef proteins" Rev. Roum. Virol. 43:95–100.

Sabatier, J.–M. et al. (1990) "Large fragments of nef–protein and gp110 envelope glycoprotein from HIV–1" Int. J. Peptide Protein Res. 35:63–72.

Choppin, J. et al. (1991) "HLA–Binding Regions of HIV–1 Proteins" The Journal of Immunology 147(2):569–574.

Kotzin B. et al., Superantigens and their porential role in human disease, Adv Immunol. 54:99–166, 1993.

Gallo et al., 1988, "HIV/HTLV gene nomenclature," Nature 333:514.

Laurence, J., 1988 "Update: HIV–1 Gene Nomenclature," AIDS Res. Human Retro. 4:vii–viii.

1998, "Instructions to Authors", J. Virol. 72(1):x–xi.

*Primary Examiner*—Laurie Scheiner
*Assistant Examiner*—Jeffrey S. Parkin
*Attorney, Agent, or Firm*—Saliwanchik, Lloyd & Saliwanchik

[57] ABSTRACT

The human immunodeficiency virus (HIV) contains, in addition to the canonical genes gag, pol, and env, an open reading frame in the 3' region of the genome that overlaps with the 3' long terminal repeat (LTR). Initial studies on the protein encoded by this ORF revealed a negative effect on HIV replication in vitro and this gene product was subsequently designated the negative factor, or Nef. The nef gene product is 25–29 kDa protein that localizes primarily to the cytoplasm of HIV-infected cells. The subject of this invention pertains to the discovery of a superantigen activity associated with this peptide and peptidic fragments derived therefrom. Superantigens are powerful T-cell mitogens that bind directly to major histocompatibility complex (MHC) class II molecules and form a binary complex with the variable β ($V_β$) region of the T-cell antigen receptor (TCR). It was demonstrated that Nef induces the rapid proliferation of human peripheral mononuclear cells and T-lymphocyte cytokine production. Nef peptidic fragments were also identified that display major histocompatibility complex (MHC) class II binding activity. These peptides can be utilized to generate suitable immune responses in the desired host.

6 Claims, 5 Drawing Sheets

METHODS FOR STIMULATING IMMUNE RESPONSES IN A HOST THROUGH THE ADMINISTRATION OF SUPERANTIGEN PEPTIDES DERIVED FROM HUMAN IMMUNODEFICIENCY VIRUS TYPE 1 NEF

CROSS-REFERENCE TO A RELATED APPLICATION

This application is a continuation-in-part of application Ser. No. 08/145,708, filed Oct. 29, 1993 now U.S. Pat. No. 5,519,114.

This invention was made with government support under National Institutes of Health grant number AI25904. The government has certain rights in this invention.

BACKGROUND OF THE INVENTION

Normally, when a person's immune system encounters a protein made by a virus or other microbe, fewer than one in 10,000 of the white blood cells known as T lymphocytes react. Although their number is small, these T lymphocytes orchestrate an attack that specifically targets the alien protein, or antigen, without harming healthy tissue. In contrast, proteins called superantigens highly activate the immune system and can cause an unproductive, even destructive, immune response.

Superantigens are the most powerful T cell mitogens known (Johnson, H. M., H. I. Magazine [1988] *Int. Arch Allergy Appl. Immunol.* 87:87–90). As explained below, these unique antigens stimulate T cells by first binding to class II major histocompatibility (MHC) molecules (Carlsson, R., H. Fischer, H. O. Sjogren [1988] *J. Immunol.* 140:2484–2488; Fleischer, B., H. Schrezenmeier [1988] *J. Exp. Med.* 167:1697–1707; Mollick, J. A., R. G. Cook, R. R. Rich [1989] *Science* 244:817–820) forming a binary complex which binds in a $V_\beta$-specific manner to the T cell antigen receptor (TCR) (Janeway, C. A., J. Yagi, P. J. Conrad, M. E. Katz, B. Jones, S. Vroegop, S. Buxser [1989] *Immunol. Rev.* 107:61–88; White, J., A. Herman, A. M. Pullen, R. Kubo, J. W. Kappler, P. Marrack [1989] *Cell* 56:27–35).

Superantigens can arouse as many as one in five T cells, most of which are useless for fighting a current infection. What is worse, certain of the activated cells may unleash an autoimmune attack which targets tissues of the host organism. At times, superantigens may even have the opposite effect: they somehow trigger the death of the cells they excite.

Scientists have gleaned much of what they understand about superantigens from studying the earliest known examples: a group of structurally related proteins called staphylococcal enterotoxins (SEs). Staphylococcal enterotoxins account for as much as 45 percent of all cases of food poisoning. It is well established that when strains of the bacterium *Staphylococcus aureus* colonize food, they secrete one or more enterotoxins, which are now named alphabetically as A, B, C, D, and E. Within hours after people ingest badly contaminated, toxin-laden food, they begin to feel weak, feverish, and nauseated. Interestingly, intestinal tissue of affected patients looks virtually normal under the microscope. The only obvious abnormality is the presence of white cells in the tissue. It has now also been found that introduction of an enterotoxin to blood triggers the proliferation of lymphocytes. Just a few hundred molecules of toxin triggers a degree of replication that surpasses what could be achieved by a billion copies of a conventional antigen—for example, a protein on the influenza virus.

Further research has documented that a small amount of an enterotoxin can yield extraordinarily high production of chemical signals known as cytolines, which are produced by the subset of T lymphocytes called helper cells. These helper T cells direct much of the immune response. The helper T cells do not attack microbes themselves; instead they rely on the cytokines to activate both cytotoxic T lymphocytes, which kill infected cells, and B lymphocytes, which secrete antibodies against antigens.

By the mid-1980s it was recognized that when a tiny amount of enterotoxin A was mixed with T lymphocytes, the collection of cells produced a huge quantity of the cytokine known as interleukin-2 (IL-2). It has also been determined that infusion of high doses of IL-2 into the circulation of cancer patients (as part of an experimental therapy) causes the very symptoms associated with food poisoning. These data indicate that enterotoxins make people ill by stimulating production of high levels of interleukin-2.

Before helper T cells can recognize conventional protein antigens, the proteins must first undergo processing by macrophages or other antigen-presenting cells (APC). These cells engulf the antigens and process them into peptides. The presenters then display the peptide antigens at the cell surface in combination with major histocompatibility complex (MHC) class II molecules. A peptide fits in a cleft on an MHC molecule. Once an antigen is displayed, the few helper cells in the body that bear receptors for the particular peptide link up with it. Each T cell is specific for one kind of peptide antigen.

Like conventional toxins, enterotoxin superantigens can arouse helper T cells only if antigen-presenting cells display the proteins to the T cells. Moreover, it is MHC class II molecules that do the presenting. Yet, unlike typical antigens, the enterotoxins bind to MHC molecules directly; they do not require uptake and processing by APC. Also, enterotoxins do not bind to the inner surface of the peptide-recognizing pocket of the MHC molecule, attaching instead to its outer surface. Then the MHC-superantigen unit contacts the T cell receptor at a site distinct from the surface that envelops conventional antigens. To be more precise, T cell receptors consist of two protein chains, alpha and beta. Both chains include structurally invariant and variable regions that participate in the binding of conventional peptide antigens. The enterotoxins are thought to link up with the beta-chain variable—or V-beta ($V_\beta$)—region, at a part not involved in the binding of typical antigens.

Each enterotoxin interacts with particular $V\beta$ types. For instance, one enterotoxin may be recognized by the variable types numbered 5 and 12, whereas another might be recognized by types 12, 15, and 18. For example, SEB has been shown to be specific for T cells bearing $V_\beta$ elements such as 7 and 8.1–8.3 in mice (Herman, A., J. W. Kappler, P. Marrack, A. M. Pullen [1991] *Ann. Rev. Immunol.* 9:745–772). Investigators estimate that every human has fewer than 30 $V_\beta$ types, although the fraction of helper T cells carrying any given type can differ from person to person. A conventional antigen can activate only the relatively few helper cells specific for that antigen. A given enterotoxin, however, can activate many times that number of helpers (having a huge variety of peptide-antigen specificities) as long as the T cells bear selected $V_\beta$ types.

Although superantigens are suspected of, at times, causing over-activation of the immune system, some evidence suggests that superantigens may also depress the immune system. T cell clones aroused by superantigens often disappear (depletion) or become inactive (anergy) after being stimulated. Staphylococcal enterotoxdns, the prototype superantigens, activate T cells bearing specific T cell antigen receptor β-chain variable region elements. Their $V_\beta$ specificity has profound implications with regard to expansion, anergy, and deletion of various T cell populations in terms of immunologic disease. It has been demonstrated that although an initial mitogenic effect is observed after in vivo administration of staphylococcal enterotoxin B (SEB), the lasting result appears to be both clonal anergy and deletion of $V_\beta$ specific peripheral T cells (Kawake, Y., A. Ochi [1991] Nature 349:245–248; Kawake, Y., A. Ochi [1990] J. Exp. Med. 172:1065–1070; Rellahan, B. L., L. A. Jones, A. M. Kruisbeek, A. M. Fry, L. A. Matis [1990] J. Exp. Med. 172:1092–1100).

Thus far, we have primarily focused on the interaction between superantigens and helper T cell activity; however, the possible deranging effects of superantigens on B cells should not be ignored. Staphylococcal enterotoxins sometimes enhance antibody production by B cells and sometimes inhibit it, depending on the initial state of immune arousal. Enhancement and suppression may each be destructive. Inhibition of antibody production can depress immune functioning. Overzealous production can lead to immune complex disorders, in which antibodies attract various components of the immune system to healthy tissue, clogging them and impeding normal function.

Interaction of the staphylococcal enterotoxins with class II molecules induces production of the cytokines tumor necrosis factor alpha (TNFα) and interleukin-1 (IL-1) by monocytes (Fischer, H., M. Dohlsten, U. Andersson, G. Hedlund, P. Ericsson, J. Hansson, H. O. Sjögren [1990] J. Immunol. 144:4663; Gjörloff, A., H. Fischer, G. Hedlund, J. Hansson, J. S. Kenney, A. C. Allison, H. O. Sjögren, M. Dohlsten [1991] Cell Immunol. 137:61). Both SEA and the related toxic shock syndrome toxin one (TSST-1) are potent inducers of TNFα and IL-1. Binding of these superantigens to MHC transduces a signal through the monocyte membrane which leads to tyrosine kinase activation and phosphorylation of multiple cytoplasmic proteins and monokine gene induction (Scholl, P. R., N. Trede, T. A. Chatila, R. S. Geha [1992] J. Immunol. 148:2237). Subsequently, monokines can have effects on T cells; for example, TNFα can further enhance human T cell proliferation (Yokota, S., T. D. Geppert, P. E. Lipsky [1988] J. Immunol. 140:531). IL-1 is an additional stimulator by increasing IL-2 secretion and IL-2 receptor expression. Both IL-1 and TNFα secretion may require the presence of T cells, particularly CD4+ 45RO+ memory T cells (Fischer et aL, supra; Gjörloff et al, supra). A variety of peptide sequences of the superantigen SEA that participate in binding to the class II MHC molecules have previously been studied (Pontzer, C. H., J. K. Russell, H. M. Johnson [1989] J. Immunol. 143:280; Pontzer, C., J. K. Russell, M. A. Jarpe, H. M. Johnson [1990] Int. Arch. Allergy Appl. Immunol. 93:107; Griggs, N. D., C. H. Pontzer, M. A. Jarpe, H. M. Johnson [1992] J. Immunol. 148:2516; Grossman, D., R. G. Cook, J. T. Sparrow, J. A. Mollick, R. R. Rich [1990] J. Exp. Med. 172:1831; Grossman, D., M. Van, J. A. Mollick, S. K. Highlander, R. R. Rich [1991] J. Immunol. 147:3274).

Superantigens have been hypothesized to be associated with a number of pathological conditions. For example, superantigen alteration of the T cell repertoire has import for immunodeficiency and autoimmunity. T cells bearing certain $V_\beta$ types have been implicated in various autoimmune conditions, including arthritis, lupus, and multiple sclerosis. It is conceivable, but not yet established, that over-activation of T cells by superantigens could play a role in certain autoimmune disorders.

Involvement of a predominant $V_\beta$ specific T cell population has been suggested for certain animal models of autoimmune disease. For example, experimental allergic encephalomyelitis (EAE) is an animal model for multiple sclerosis. Multiple sclerosis (MS) is a chronic, often disabling disease that attacks the central nervous system, damaging the protective coating that surrounds nerve fibers. EAE is mediated by $V_\beta 8.2^+$, CD4+ T cells in PL/J mice after injection with myelin basic protein (MBP). This limited heterogeneity of TCR usage has implicated the involvement of $V_\beta 8.2^+$, CD4+ T cells in EAE in PL/J mice immunized with rat myelin basic protein (Acha-Orbea, H., D. J. Mitchell, L. Timmerman, D. C. Wraith, G. S. Tausch, M. K Waldon, S. S. Zamvil, H. O. McDevitt, L. Steinman [1988] Cell 54:263–273).

Recently, several novel immunological approaches have been explored relevant to autoimmune diseases such as EAE in mice and rats and lupus nephritis in MRL/1 pr mice. Many have been directed toward blocking the function of the effector CD4+ T cell which has been shown to exhibit $V_\beta$ isotype restriction in EAE. These approaches have included the use of anti-TCR antibodies (Acha-Orbea et al., supra), synthetic TCR peptides (Offner, H., G. A. Hashim, A. A. Vandenbark [1991] Science 251:430–432) and superantigen treatment (Kim, C., K. A. Siminovitch, A. Ochi [1991] J. Exp. Med. 174:1431–1437).

Superantigens are also associated with retroviruses such as mouse mammary tumor virus (MMTV), and possibly human immunodeficiency virus (HIV), the virus responsible for AIDS. It has recently been reported that two exogenous strains of MMTV encode retroviral superantigens in the open reading frames (ORFs) of the 3' Long Terminal Repeat (LTR) of the viral genome (Pullen, A. M., Y. Choi, E. Kushnir, J. Kappler, P. Marrack [1992] J. Exp. Med. 175:41–47; Choi, Y., P. Marrack, J. Kappler [1992] J. Exp. Med. 175:847–851). There is preliminary evidence that the HIV genome may also encode a superantigen. It has been suggested that an HIV superantigen may target a subpopulation of CD4+ T cells for HIV viral replication (Laurence, J., A. S. Hodtsev, D. N. Posnett [1992] Nature 358:255–259). HIV infection also results in the programmed cell death of CD4+ T cells (apoptosis), both in vitro and in vivo, possibly as a result of an HIV protein with superantigen properties (Gougeon, M-L., L. Montagnier [1993] Science 260:1269–1270). Feline immunodeficiency virus (FIV) is a lentivirus which has been described extensively in the literature. See, for example, Kiyomasu, Takahiro, et al. (1991) "Identification of Feline Immunodeficiency Virus rev Gene Activity" Journal of Virology 65(8):4539–4542, and references cited therein. There has also been speculation that the human spumaretrovirus (HSRV) expresses a superantigen ("Molecular Biology of the Human Spumavirus," in Human Retroviruses, B. R. Cullen, ed., Oxford University Press, Oxford and New York, 1993, pp. 205–206).

Like many viruses, including MMTV and FIV, the HIV genome has a 3' Long Terminal Repeat. Initial studies indicated that a protein encoded by an ORF in the 3' LTR had negative effects on HIV replication in vitro, and hence was designated Negative Factor (Nef). Nef is a 25–29 kD protein that is mainly located in the cytoplasm of HIV-infected cells, but is also associated with the plasma membrane (Allan, J. S., J. E. Coligan, T-H. Lee, M. F. McLane, P. J. Kanki, J. E. Groopman, M. Essex [1985] Science 230:810–813). The role of NeF in retroviral pathogenesis has been studied (Laurent, A. G., A. G. Hovanessian, Y. Riviere, b. Krust, A. Regnault, L. Montagnier, A. Findeli, M. P. Kieny, B. Guy [1990] J. Gen. Virol. 71:2273–2281). There are no reports that suggest Nef as a superantigen.

BRIEF SUMMARY OF THE INVENTION

The subject invention concerns the discovery of specific superantigen proteins and peptides and the use of these proteins and peptides as diagnostic reagents and in methods for modulating immune responses. More specifically, the subject invention concerns the discovery of superantigen proteins encoded in open reading frames (ORF) of the 3' Long Terminal Repeat (LTR) region of retroviruses. Specifically exemplified herein are superantigen proteins from the mouse mammary tumor virus (MMTV), feline immunodeficiency virus (FIV) and human immunodeficiency virus-1 (HIV-1).

A further aspect of the invention is the discovery of specific superantigen peptide fragments of the retroviral superantigen proteins. The superantigen nature of these peptides can be manifested in their ability to bind to known superantigen receptor sites, their reactivity with antibodies raised to superantigens, or their own ability to elicit an immune response characteristic of superantigens. For example, the MMTV and HIV-derived superantigen peptides of the subject invention are able to block the binding of $^{125}$I-labelled superantigen staphylococcal enterotoxin A (SEA) to class II MHC-bearing cells by binding to a region on the MHC molecule where SEA normally binds. An FIV superantigen peptide has also been discovered which reacts with antibodies known to be associated with FIV infection.

In one embodiment of the subject invention, we have identified a superantigen peptide, designated herein as MMTV ORF (76–119) [SEQ ID NO. 1], derived from the MMTV 3' LTR ORF superantigen. We have discovered that this peptide binds to the same region on the β-chain of class II MHC molecules as does the SEA superantigen. As described herein, the MMTV ORF superantigen peptide is useful for inducing an immune response in vitro or in an animal in need of such a response.

Another aspect of the subject invention is the discovery of an FIV superantigen which has not previously been isolated or characterized. The FIV superantigen is encoded by a sequence within the 3' LTR ORF of the genome of the FIV virus. We have also identified two peptides, FIV ORF4 (1–30) [SEQ ID NO. 10] and FIV ORF4 (21–55) [SEQ ID NO. 11], derived from the 3' LTR ORF4 of FIV, that are recognized by the antisera of both FIV-vaccinated and FIV-infected cats. In addition, the FIV ORF4(1–30) [SEQ ID NO. 10] peptide can be used as an immunoaffinity reagent to purify viral neutralizing antibodies from FIV-infected cat sera. Thus, the FIV ORF4 superantigen peptides of the subject invention can be used to detect FIV-induced antibodies and as an immunoaffinity reagent to purify anti-FIV antibodies. These peptides can also be used to raise an immune response.

The HIV-1 superantigen of the subject invention corresponds to the HIV-1 Negative Factor (Nef) protein which has never before been recognized to have superantigen properties. We have discovered that the HIV-1 NeF protein induces a rapid proliferation of human peripheral mononuclear cells and that T cells are activated by Nef to produce cytokines. Also, we have identified a peptide fragment of the HIV-1 Nef protein, designated here as HIV-1 Nef(123–160) [SEQ ID NO. 18], which binds to human class II MHC. Thus, in one embodiment of the subject invention, the Nef superantigen protein or peptide can be used to raise an immune response in an animal in need of such a response.

The ability of peptide superantigen agonists to alter the T cell repertoire has implications for the treatment of a variety of immunologic disease states such as immunodeficiency and autoimmunity. While immunotherapy using the whole superantigen molecule could produce non-specific effects and potentially undesirable side effects, peptide agonists and antagonists of superantigen function can target components of the immune system, alter function, and achieve therapeutic ends. The peptides can also be used in diagnostic procedures to detect the presence of superantigens or antibodies that are immunoreactive with superantigens.

BRIEF DESCRIPTION OF THE SEQUENCES

Figure 1:
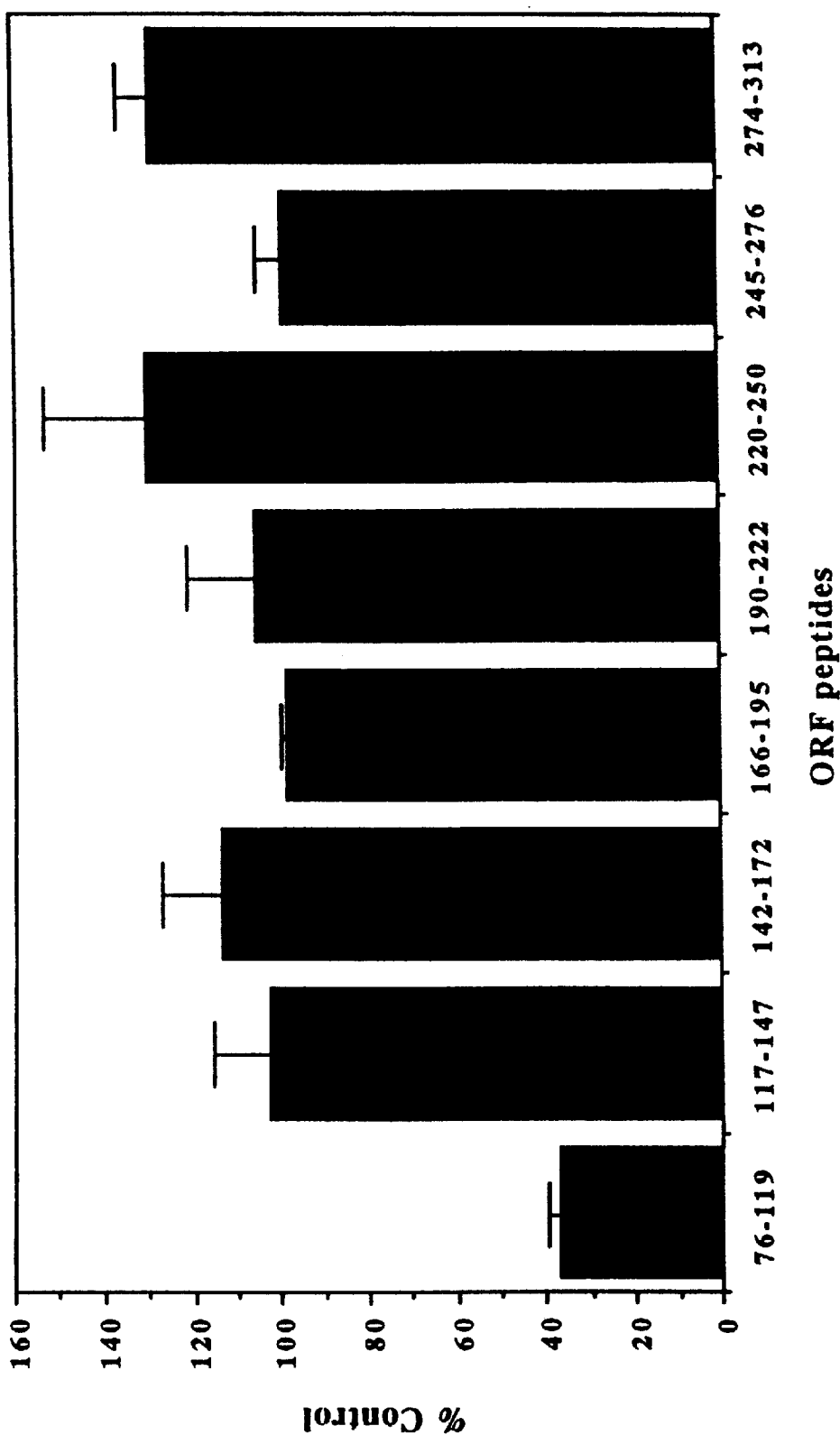
FIG. 1. Competitive binding of MMTV ORF peptides to mouse A20 cells. Competitor peptides were used at a final concentration of 200 μM. $^{125}$I-SEA was added at a final concentration of 2.5 nM. Binding of $^{125}$I-SEA in the absence of competitors was 6,384±400 CPM. The data presented represent the mean of three individual experiments each performed in duplicate. Each bar represents the mean percent reduction of SEA control binding in the presence of ORF peptides ±standard deviation.

SEQ ID NO. 1 is the amino acid sequence of an MMTV ORF peptide designated MMTV ORF(76–119).

SEQ ID NO. 2 is the amino acid sequence of an MMTV ORF peptide designated MMTV ORF(117–147).

SEQ ID NO. 3 is the amino acid sequence of an MMTV ORF peptide designated MMTV ORF(142–172).

SEQ ID NO. 4 is the amino acid sequence of an MMTV ORF peptide designated MMTV ORF(166–195).

SEQ ID NO. 5 is the amino acid sequence of an MMTV ORF peptide designated MMTV ORF(190–222).

SEQ ID NO. 6 is the amino acid sequence of an MMTV ORF peptide designated MMTV ORF(220–250).

SEQ ID NO. 7 is the amino acid sequence of an MMTV ORF peptide designated MMTV ORF(245–276).

SEQ ID NO. 8 is the amino acid sequence of an MMTV ORF peptide designated MMTV ORF(274–313).

SEQ ID NO. 9 is a scrambled amino acid sequence of MMTV ORF(76–119) [SEQ ID NO. 1] and is designated MMTV ORF(76–119) scrambled.

SEQ ID NO. 10 is the amino acid sequence of an FIV ORF4 peptide designated FIV ORF4 (1–30).

SEQ ID NO. 11 is the amino acid sequence of an FIV ORF4 peptide designated FIV ORF4 (21–55).

SEQ ID NO. 12 is the amino acid sequence of an FIV ORF4 peptide designated FIV ORF4 (31–65).

SEQ ID NO. 13 is the amino acid sequence of an FIV ORF4 peptide designated FIV ORF4 (51–71).

SEQ ID NO. 14 is the amino acid sequence of an HIV-1 Nef peptide designated HIV-1 Nef (1–38).

SEQ ID NO. 15 is the amino acid sequence of an HIV-1 Nef peptide designated HIV-1 Nef (31–65).

SEQ ID NO. 16 is the amino acid sequence of an HIV-1 Nef peptide designated HIV-1 Nef (62–99).

SEQ ID NO. 17 is the amino acid sequence of an HIV-1 Nef peptide designated HIV-1 Nef (93–132).

SEQ ID NO. 18 is the amino acid sequence of an HIV-1 Nef peptide designated HIV-1 Nef (123–160).

SEQ ID NO. 19 is the amino acid sequence of an HIV-1 Nef peptide designated HIV-1 Nef (156–186).

SEQ ID NO. 20 is the amino acid sequence of an HIV-1 Nef peptide designated HIV-1 Nef (182–206).

DETAILED DESCRIPTION OF THE INVENTION

The subject invention pertains to new compositions and methods utilizing viral superantigens and superantigen peptides. Specifically, these superantigens and superantigen peptides have been discovered within the 3' long terminal repeat (LTR) of several retroviruses. In specific embodiments of the subject invention, we have discovered superantigens and superantigen peptides from the mouse mammary tumor virus (MMTV), feline immunodeficiency virus (FIV), and human immunodeficiency virus (HIV).

This invention is the first report of specific superantigen sequences from either FIV or HIV, and it is the first report of any superantigen peptide antagonists and agonists from retroviruses. The peptides described herein are particularly advantageous because they facilitate specific manipulation of the immune system. Because of the involvement of autoimmune processes in various disease states such as diabetes, multiple sclerosis, lupus, and rheumatoid arthritis, the peptides of the subject invention provide advantageous therapeutic agents. These peptides can also be used in diagnosing and treating various autoimmune and retroviral-induced disorders. The peptides can also be used to produce antagonists to proteins having superantigen activity, and to produce polyclonal and monoclonal antibodies that specifically bind to the superantigen from which the peptide was derived.

The term "superantigen" is being used herein as denoting a molecule that would typically have the following properties: (1) A molecule that binds directly to class II MHC on antigen presenting cells (APC) in a region outside of the antigen-binding groove on the MHC molecule, (2) wherein the superantigen does not require processing by the APC, (3) which then binds as a binary complex to the T cell antigen receptor in a Vβ-specific manner, and (4) thereby activates T cells bearing those specific Vβ types. Typically, the superantigen will effectively compete with Staphylococcal enterotoxins for binding to a class II MHC molecule.

As used herein, the term "anergy" refers to the inactivation of a cell after being stimulated by a superantigen.

The MMTV superantigen is encoded in an open reading frame (ORF) of the 3' Long Terminal Repeat (LTR) of the MMTV viral genome. The MMTV superantigen is believed to be a 45 kD type II integral membrane protein with a glycosylated extracellular C-terminus and an intracellular N-terminus (Choi, Y., P. Marrack, J. W. Kappler [1992] *J. Exp. Med.* 175:847–851). As described in more detail below, overlapping peptides corresponding to the amino acid sequence of the predicted extracellular domain of the MMTV ORF superantigen were synthesized (designated here as MMTV ORF): MMTV ORF(76–119) [SEQ ID NO. 1], MMTV ORF(117–147) [SEQ ID NO. 2], MMTV ORF (142–172) [SEQ ID NO. 3], MMTV ORF(166–195) [SEQ ID NO. 4], MMTV ORF(190–222) [SEQ ID NO. 5], MMTV ORF(220–250) [SEQ ID NO. 6], MMTV ORF(245–276) [SEQ ID NO. 7], and MMTV ORF(274–313) [SEQ ID NO. 8]. These peptides are shown in Table 1.

TABLE 1

Amino acid sequences of MMTV ORF peptides

| ORF peptide | Sequence |
|---|---|
| MMTV ORF(76–119) | SEQ ID NO. 1 - DSFNNSSVQDYNLNDSENSTFLLGQGPQPTSSYKPHRLCPSEIE |
| MMTV ORF(117–147) | SEQ ID NO. 2 - EIEIRMLAKNYIFTNETNPIGRLLIMMLRNE |
| MMTV ORF(142–172) | SEQ ID NO. 3 - MMLRNESLSFSTIFTQIQRLEMGIENRKRRS |
| MMTV ORF(166–195) | SEQ ID NO. 4 - ENRKRRSTSVEEQVQGLRASGLEVKRGKRS |
| MMTV ORF(190–222) | SEQ ID NO. 5 - KRGKRSALVKIGDRWWQPGTYRGPYIYRPTDAP |
| MMTV ORF(220–250) | SEQ ID NO. 6 - DAPLPYTGRYDLNFDRWVTVNGYKVLYRSLP |
| MMTV ORF(245–276) | SEQ ID NO. 7 - LYRSLPFRERLARARPPWCVLSQEEKDDMKQQ |
| MMTV ORF(274–313) | SEQ ID NO. 8 - KQQVHDYIYLGTGMIHWKVFYNSREEAKRHIIEHIKALP |
| MMTV ORF(76–119) scrambled | SEQ ID NO. 9 - PNSNEGLSQQSTDPSPHNFILSNENSYPCYSLLGDVQREDSTKF |

The peptides shown in Table 1 were tested at a concentration of 200 μM for their ability to compete with $^{125}$I-SEA for binding to A20 cells, a cell line that expresses I-A$^d$ and I-E$^d$. MMTV ORF(76–119) [SEQ ID NO. 1] reduced the binding of $^{125}$I-SEA by approximately 63% (FIG. 1). None of the other MMTV ORF peptides were able to reduce $^{125}$I-SEA binding at the concentration tested. In a dose response study, the MMTV ORF(76–119) [SEQ ID NO. 1] peptide was able to reduce $^{125}$I-SEA binding to A20 cells by approximately 50% at concentrations as low as 20 μM. Additionally, a radioimmunoassay was performed to determine if the competition observed with MMTV ORF (76–119) [SEQ ID NO. 1] was due to the direct binding of the peptide to the A20 cells. $^{125}$I-MMTV ORF(76–119) [SEQ ID NO. 1] did bind to the A20 cells and was effectively inhibited by both unlabeled SEA and unlabeled MMTV ORF(76–119) [SEQ ID NO. 1]. Unlabeled SEA and MMTV ORF(76–119) [SEQ ID NO. 1] competed with $^{125}$I-MMTV ORF(76–119) [SEQ ID NO. 1] in a similar manner, although SEA was a more potent competitor. SEA reduced $^{125}$I-MMTV ORF(76–119) [SEQ ID NO. 1] binding by 50% at a concentration of 1.8 μM as compared to 25 μM for unlabeled MMTV ORF(76–119) [SEQ ID NO. 1]. An MMTV ORF(76–119) scrambled [SEQ ID NO. 9] peptide did not compete, indicating that MMTV ORF(76–119) [SEQ ID NO. 1] binding to A20 cells is sequence specific. Toxic shock syndrome toxin-1 (TSST-1) did not compete with $^{125}$I-MMTV ORF(76–119) [SEQ ID NO. 1], whereas the staphylococcal enterotoxin B (SEB) competed less effectively than SEA. This evidence indicates that MMTV ORF (76–119) [SEQ ID NO. 1] binds to murine class II molecules at a region where SEA also binds.

Binding experiments using class II-positive (A20 cells) and class II- negative (L cells) cell lines demonstrated that binding of MMTV ORF(76–119) [SEQ ID NO. 1] peptide to the class II-negative L cell line is insignificant in comparison to MMTV ORF(76–119) [SEQ ID NO. 1] binding to A20 cells. In addition, antibodies that specifically bind to class II antigens were able to significantly block binding of the MMTV ORF(76–119) [SEQ ID NO. 1] peptide A20 cells, whereas antibodies specific for class I MHC did not block binding of the peptide. When polyclonal I-A$^d$ and Ia.7 antibodies were used in combination, the binding of the MMTV ORF(76–119) [SEQ ID NO. 1] peptide to A20 cells was reduced by 73%. These antibodies can be obtained from the NIH.

A competitive radioimmunoassay using a peptide corresponding to amino acid residues 60–90 of the class II MHC β-chain was performed to directly determine whether MMTV ORF(76–119) [SEQ ID NO. 1] binds to the β1 helix of the I-A molecule, the same region that SEA binds to on the molecule. SEA and MMTV ORF(76–119) [SEQ ID NO. 1] competed with both $^{125}$I-SEA and $^{125}$I-MMTV ORF (76–119) [SEQ ID NO. 1] for binding to the I-Aβ$^b$(60–90) peptide in a manner similar to the competition observed on whole cells. Therefore, the data indicate that, despite the diverse origins of SEA and MMTV superantigens, SEA protein and MMTV ORF(76–119) [SEQ ID NO. 1] peptide bind to a similar region on the β-chain of murine class II MHC molecules, and, thus, the MMTV ORF peptide is a powerful tool for modulation of the immune response.

The subject invention further concerns the discovery of a superantigen and superantigen peptides from the feline immunodeficiency virus (FIV). The FIV ORF4 encodes a protein consisting of 71 amino acid residues. However, the protein product of this gene has never been shown to be expressed. Four overlapping peptides corresponding to the entire sequence of the FIV ORF4 which is found in the 3' Long Terminal Repeat region of FIV were synthesized (designated here as FIV ORF4): FIV ORF4(1–30) [SEQ ID NO. 10], FIV ORF4(21–55) [SEQ ID NO. 11], FIV ORF4 (31–65) [SEQ ID NO. 12] and FIV ORF4(51–71) [SEQ ID NO. 13]. These peptides are shown in Table 2.

TABLE 2

FIV ORF4 peptide sequence

| Peptide | Sequence |
| --- | --- |
| FIV ORF4 (1–30) | SEQ ID NO. 10 - GKRKRQRRRRKKKAFKRMMTELEDRFRKLF |
| FIV ORF4 (21–55) | SEQ ID NO. 11 - ELEDRFRKLFGTTSTTGDSTVDSEDEPPKKEKRVD |
| FIV ORF4 (31–65) | SEQ ID NO. 12 - GTTSTTGDSTVDSEDEPPKKEKRVDWDEYWNPEEI |
| FIV ORF4 (51–71) | SEQ ID NO. 13 - EKRVDWDEYWNPEEIERMLM |

Each FIV ORF4 peptide of the subject invention was tested in an ELISA assay to determine whether antisera from cats vaccinated with FIV, and having high viral-neutralizing titers, would react with any of the ORF4 peptides. Serum from a virus-vaccinated cat showed high reactivity to FIV ORF4(1–30) [SEQ ID NO. 10], but significantly less reactivity to FIV ORF4(21–55) [SEQ ID NO. 11]. There was no reactivity to either of the C-terminal peptides. A similar pattern of reactivity was observed with sera from a cell-vaccinated cat, although the reactivity was weaker than with the virus-vaccinated cat sera. Pooled sera from control cats did not react with any of the ORF4 peptides.

Figure 3:
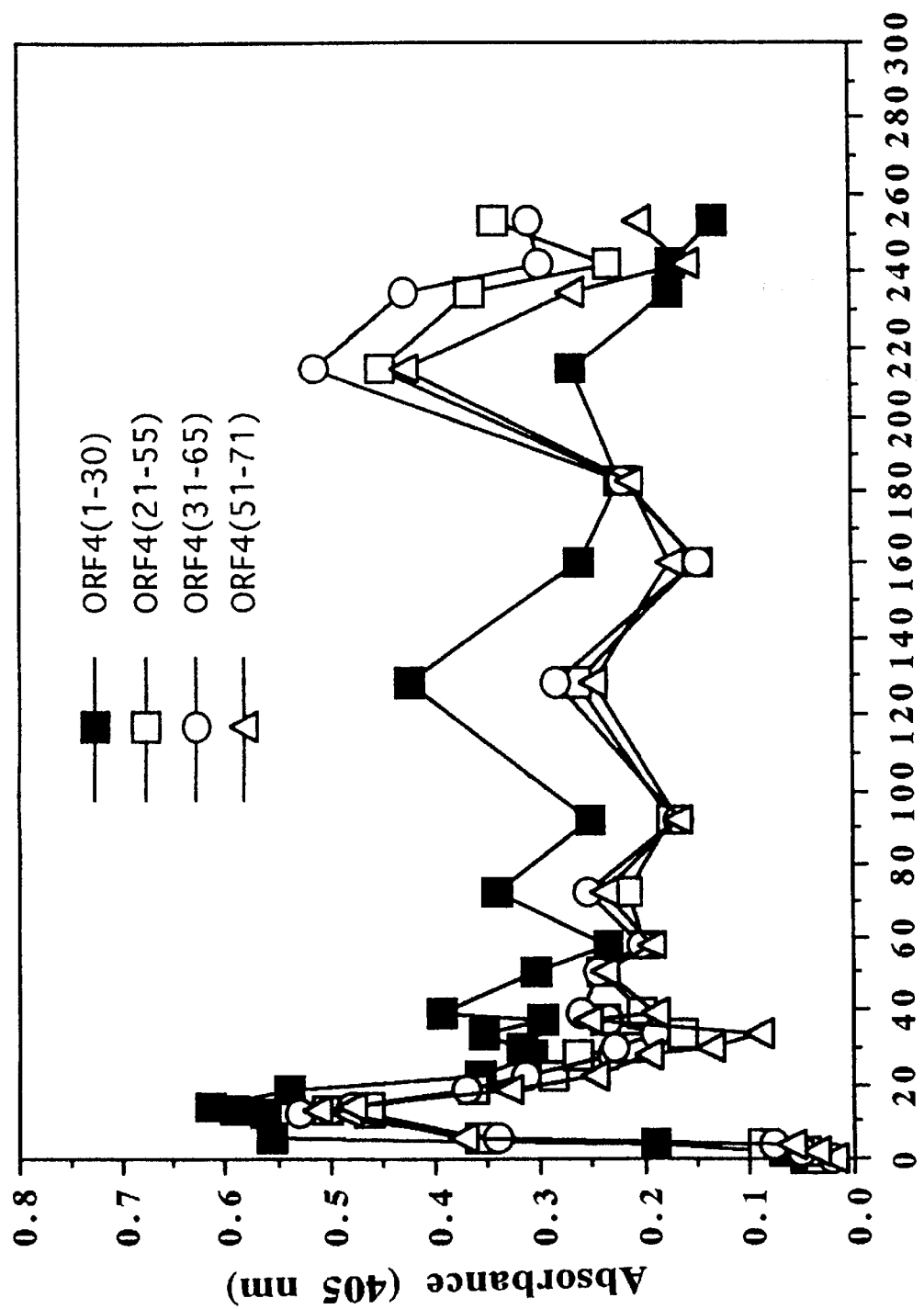
FIG. 3. ELISA reactivity of different FIV ORF4 peptides to pooled serum from FIV (Petaluma strain) infected cats drawn at different times post infection (pi).

The reactivity of pooled antisera from cats infected with FIV (Petaluma strain), drawn at various intervals post–infection, was tested for reactivity to the FIV ORF4 peptides. All four of the ORF4 peptides reacted with the antisera. Reactivity to all four peptides peaked at 10 weeks post-infection, followed by a decline to a plateau level. However, a second peak of reactivity for all of the ORF4 peptides, except FIV ORF4(1–30) [SEQ ID NO. 10], was observed with antisera drawn at about 220 weeks post-infection (FIG. 3).

Figure 4:
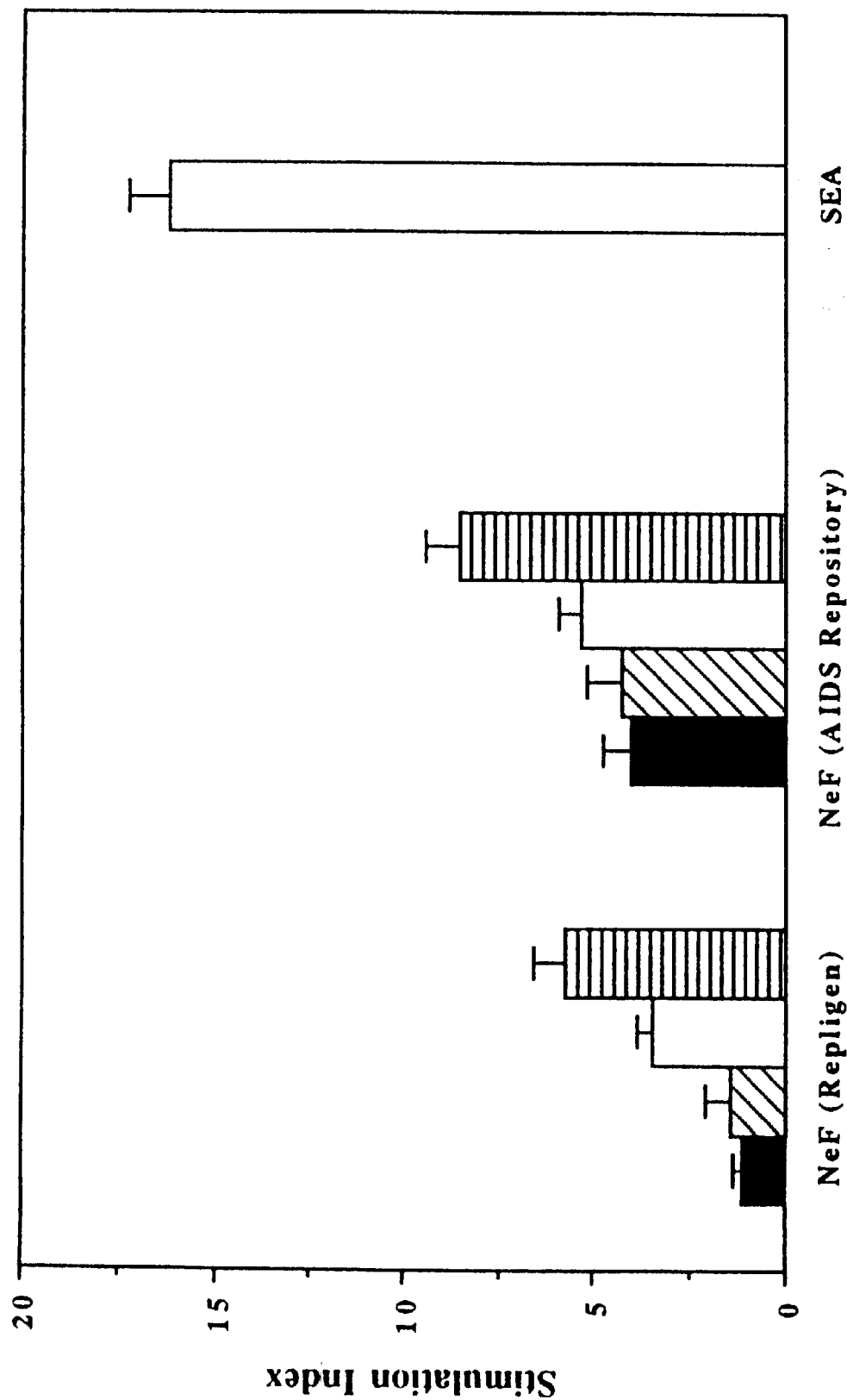
FIG. 4. Proliferation of human mononuclear cells in response to NeF and SEA. NeF obtained from Repligen and the NIH AIDS Research and Reference Reagent Program were tested at various concentrations: ■, 30 ng/ml; ▨, 100 ng/ml; □, 300 ng/ml; and ▤, 1000 ng/ml. SEA was tested at 300 ng/ml. Cultures were harvested 96 hours after initiation of culture. Proliferation of cells in the absence of stimulation was 1331±167.

The subject invention further concerns the discovery of a superantigen and superantigen peptides from the human immunodeficiency virus (HIV-1). Specifically, it has been discovered that the HIV-1 Negative Factor (Nef) is a superantigen. The HIV-1 Nef protein is one of the earliest proteins synthesized during viral replication. The HIV-1 Nef protein was tested at various concentrations in a proliferation assay to determine its effects on human peripheral mononuclear cells (PMNC's). NeF protein increased cell proliferation several fold over basal level when measured at 96 hours after initiation of the cell culture. (FIG. 4).

The same approach used for the MMTV and FIV peptides was used to synthesize overlapping peptides corresponding to the sequence of the HIV-1 NeF protein (designated here as HIV-1 Nef): HIV-1 Nef(1–38) [SEQ ID NO. 14], HIV-1 Nef(31–65) [SEQ ID NO. 15], HIV-1 Nef(62–99) [SEQ ID NO. 16], HIV-1 Nef(93–132) [SEQ ID NO. 17], HIV-1 Nef(123–160) [SEQ ID NO. 18], HIV-1 Nef(156–186) [SEQ ID NO. 19]and HIV-1 Nef(182–206) [SEQ ID NO. 20]. These peptides are shown in Table 3.

directly to class II MHC molecules, the known receptors for superantigens on antigen-presenting cells.

As discussed above, the Nef protein is capable of inducing a proliferative response in PMNCs. Nef peptides were tested using the same cell proliferation assay to determine their effect on superantigen-induced cell proliferation. Nef (123–160) [SEQ ID NO. 18] and Nef(156–186) [SEQ II) NO. 19] peptides were tested with Nef, SEA, anti-IgM and ConA (Table 4).

TABLE 3

Amino acid sequences of HIV-1 Nef peptides

| NeF PEPTIDE | SEQUENCE |
| --- | --- |
| HIV-1 Nef (1–38) | SEQ ID NO. 14 - MGGKWSKSSVVGWPTVRERMRRAEPAADGVGAASRDLE |
| HIV-1 Nef (31–65) | SEQ ID NO. 15 - GAASRDLEKHGAITSSNTAATNAACAWLEAQEEEE |
| HIV-1 Nef (62–99) | SEQ ID NO. 16 - EEEEVGFPVTPQVPLRPMTYKAAVDLSHFLKEKGGLEG |
| HIV-1 Nef (93–132) | SEQ ID NO. 17 - EKGGLEGLIHSQRRQDILDLWIYHTQGYFPDWQNYTPGPG |
| HIV-1 Nef (123–160) | SEQ ID NO. 18 - DWQNYTPGPGVRYPLTFGWCYKLVPVEPDKVEEANKGE |
| HIV-1 Nef (156–186) | SEQ ID NO. 19 - NKGENTSLLHPVSLHGMDDPEREVLEWRFD |
| HIV-1 Nef (182–206) | SEQ ID NO. 20 - EQRFDSRLAFHHVARELHPEYFKNC |

Figure 5:
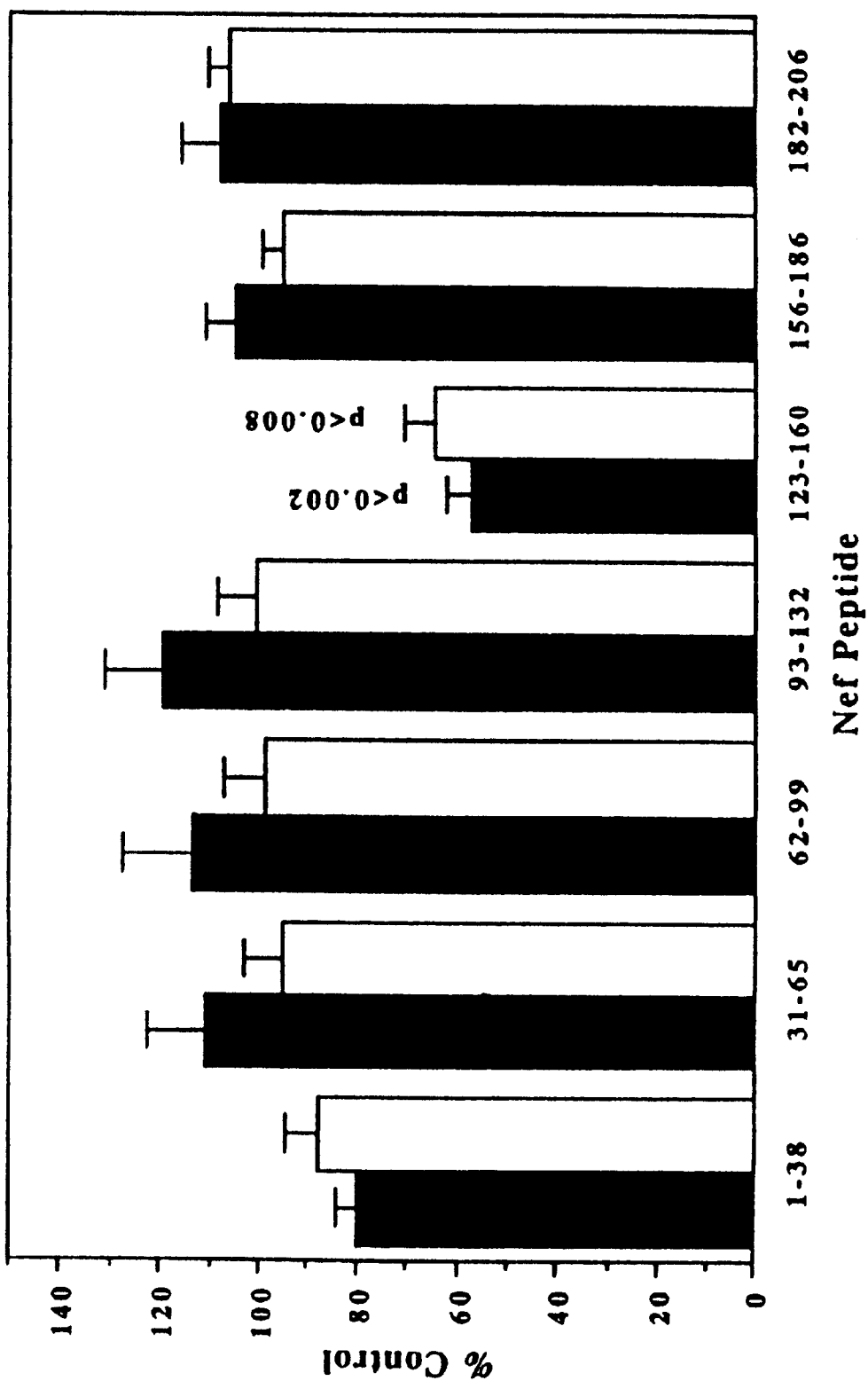
FIG. 5. Blockage of $^{125}$I-SEA binding to Raji and DR1-transfected L cells by HIV-1 NeF peptides. HIV-1 Nef peptides were used at a final concentration of 300 μM. $^{125}$I-SEA was used at a final concentration of 2 nM. $10^5$ Raji or DR1-transfected L cells were used per tube. Binding of $^{125}$I-SEA to Raji and DR1-transfected L cells in the absence of competitors was 31,469±2292 and 5,708±41 CPM, respectively. Data represent the mean percent of control of three individual experiments, each performed in duplicate. Bars represent binding to Raji (■) and DR1-transfected L cells (□) in the presence of Nef peptides ±SD.

The HIV-1 Nef(123–160) [SEQ ID NO. 18] peptide was found to block the binding of $^{125}$I-SEA to Raji cells, a human cell line that expresses class II MHC molecules on its surface (FIG. 5). At the highest concentration tested, 300 μM, HIV-1 Nef(123–160) [SEQ ID NO. 18] peptide reduced the binding of $^{125}$I-SEA to Raji cells by approximately 40%, and competed with SEA in a dose-dependent manner. HIV-1 Nef(1–38) [SEQ ID NO. 14] and HIV-1 Nef(31–65) [SEQ ID NO. 15] had slight inhibitory effects on $^{125}$I-SEA binding when the peptides were present at a concentration of 300 μM. Unlabeled SEA reduced $^{125}$I-SEA binding by 50% at a concentration of 0.2 μM, a reduction that is consistent with the reported Kd of SEA for HLA molecules.

The HIV-1 Nef(123–160) [SEQ ID NO. 18] peptide was also tested to determine whether there was direct binding to Raji cells. Unlabeled HIV-1 Nef(123–160) [SEQ ID NO. 18] reduced $^{125}$I-HIV-1 Nef(123–160) [SEQ ID NO. 18] binding by 50% at a concentration of 30 μM, and unlabeled SEE reduced $^{125}$I-HIV-1 Nef(123–160) [SEQ ID NO. 18] binding by 50% at a concentration of 2 μM. Unlabeled SEA did not inhibit $^{125}$I-HIV-1 Nef(123–160) [SEQ ID NO. 18] binding as well as SEE, but it was more effective than $SEC_1$ or SEB. This data demonstrates that HIV-1 Nef(123–160) [SEQ ID NO. 18] peptide competes for sites on MHC class II molecules that are more closely associated with sites where SEE binds to the class II molecule than sites where the other SEs bind.

Monoclonal antibodies specific to class I and class II antigens were used to determine which receptors the $^{125}$I-HIV-1 Nef(123–160) [SEQ ID NO. 18] peptide was binding on Raji cells. Clone L243, a monoclonal antibody specific for HLA-DR, reduced $^{125}$I-HIV-1 Nef(123–160) [SEQ ID NO. 18] binding by about 35%. Anti-HLA-DR monoclonal antibodies from clone L227 reduced peptide binding, but not as effectively as clone L243. Antibodies to class I antigens had no effect on $^{125}$I-HIV-1 Nef(123–160) [SEQ ID NO. 18] binding. These antibodies are available from Becton Dickinson, Mountain View, Calif. The data indicate that HIV-1 Nef(123–160) [SEQ ID NO. 18] peptide binds

TABLE 4

Ability of Nef(123–160) to specifically block proliferation of human peripheral mononuclear cells by Nef and SEA

| Cells cultured in the presence of: | SI ± sd |
| --- | --- |
| Nef | 22.6 ± 0.3 |
| Nef + Nef(123–160) | 3.9 ± 2.2 |
| Nef + Nef(156–186) | 19.6 ± 0.2 |
| SEA | 17.6 ± 3.3 |
| SEA + Nef(123–160) | 6.2 ± 0.4 |
| SEA + Nef(156–186) | 16.6 ± 2.1 |
| Anti-IgM | 18.0 ± 1.6 |
| Anti-IgM + Nef(123–160) | 14.1 ± 0.5 |
| Anti-IgM + Nef(156–186) | 20.0 ± 1.8 |
| ConA | 6.0 ± 0.4 |
| ConA + Nef(123–160) | 4.5 ± 0.4 |
| ConA + Nef(156–186) | 5.2 ± 1.6 |

Nef and SEA were used at 30 ng/ml. Anti-IgM and concanavalin A (ConA) are mitogens for B and T cells, respectively, and were used at 10 μg/ml. Nef peptides were used at. 100 μM.

The Nef(123–160) [SEQ ID NO. 18] peptide inhibited PMNC cell proliferation induced by both the Nef protein and SEA. However, the Nef(156–186) [SEQ ID NO. 19] peptide did not significantly inhibit either Nef- or SEA-induced cell proliferation. Neither peptide significantly inhibited the proliferation of cells induced by the non-superantigen reagents, anti-IgM and ConA. These results demonstrate that Nef and SEA-induced proliferation of PMNC can be specifically inhibited using the Nef(123–160) [SEQ ID NO. 18] peptide.

The capacity of Nef protein to induce cell proliferation was also tested on whole human PMNC and fractionated PMNC. Human PMNC were purified into antigen-presenting cells (APC) and T cell fractions. APC were inactivated with paraformaldehyde in order to eliminate the antigen processing capabilities of the APC. Nef protein, SEA and ConA were then tested on whole PMNC, APC only, T cell only, or a mixture of APC and T cells (Table 5).

TABLE 5

Superantigen Properties of Nef

| Cells | SI ± sd |
|---|---|
| Whole PMNC + Nef | 26.4 ± 6.7 |
| APC + Nef | 1.1 ± 0.2 |
| T cells + Nef | 1.4 ± 0.1 |
| APC + T cells + Nef | 3.8 ± 0.4 |
| Whole PMNC + SEA | 164.1 ± 39.2 |
| APC + SEA | 1.6 ± 0.2 |
| T cells + SEA | 1.5 ± 0.3 |
| APC + T cells + SEA | 24.2 ± 5.7 |
| Whole PMNC + ConA | 178.7 ± 25.1 |
| APC + ConA | 0.9 ± 0.1 |
| T cells + ConA | 32.6 ± 7.7 |
| APC + T cells + ConA | 40.7 ± 4.3 |

Nef used at 50 µg/ml. SEA was used at 100 ng/ml. ConA was used at 10 µg/ml. APC and T cells were cultured at a ratio of 3:1 (APC:T cells).

Nef protein, SEA and ConA all induced a proliferative response in whole PMNC. Neither Nef nor SEA induced significant proliferation of the purified T cell fraction. ConA did induce proliferation of the purified T cell fraction.

When APC and T cells were reconstituted back together, both Nef and SEA induced proliferation of cells. Although the proliferative level was lower for Nef in comparison to SEA, the ratio of the stimulation index for whole PMNC versus reconstituted APC/T cells was approximately the same for both Nef and SEA (6.94 and 6.78, respectively). This data demonstrates that, like other superantigens such as SEA, Nef protein can induce proliferation of T cells cultured in the presence of APC and that antigen processing by the APC is not required.

In addition to inducing proliferation of T cells, superantigens also induce T cells to produce lymphokines such as interferon gamma (IFNγ) and interleukin-2 (IL-2). Whole PMNC were treated with either Nef protein, SEA or ConA and then culture supernatants tested for the production of IFN at 24, 48, 72 and 96 hours after treatment (Table 6).

TABLE 6

Induction of IFNγ by Nef

| Whole PMNC stimulated with: | IFNγ (U/ml) at: | | | |
|---|---|---|---|---|
| | 24 H | 48 h | 72 h | 96 h |
| SEA | 55 ± 7 | 550 ± 141 | 3000 | 2000 |
| Nef | <10 | 60 | 550 ± 141 | 1500 ± 707 |
| ConA | 10 | 350 ± 71 | 400 ± 141 | 150 ± 71 |

SEA induced maximal IFN production at 72 hours. Nef protein induced maximal IFN production at 96 hours. ConA activation of the cells also induced IFNγ production but at levels much lower than that of Nef or SEA.

Antibodies specific for either IFNα or IFNγ were used to determine the type of IFN induced by the PMNC after treatment with Nef, SEA and ConA. Treatment of the induced culture supernatants with anti-IFNα antibody had no effect on IFN titer of the sample, whereas treatment with anti-IFNγ antibody substantially decreased the IFN titer of the sample. Thus, the predominant IFN activity induced by Nef and SEA is IFNγ. Induction of IFNγ, a T-cell product, further demonstrates the superantigen properties of the Nef protein.

The discovery of peptide antagonists and agonists, especially of T cell function, is highly unexpected. As a condition of activity, the peptide must bind to MHC and TcR, and thus compete for binding with a native superantigen molecule. Use of synthetic peptide agonists and antagonists rather than the whole superantigen molecule offers advantages such as a lack of side effects and targeting of immune system components. Also, specific amino acid residues can be easily and rapidly modified to allow for generation of more effective agonists or antagonists.

As those skilled in the art can readily appreciate, there can be a great number of natural variants of retroviral sequences, in addition to those variants that can be artificially created by the skilled artisan in the lab. The sequences of naturally-occurring variants can be readily obtained from the Los Alamos Database on Human Retroviruses. The proteins and peptides of the subject invention encompasses those specifically exemplified herein, as well as any natural variants thereof, as well as any variants which can be created artificially. Of particular interest are the conserved regions of retroviral superantigen sequences.

The peptides claimed according to the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 15 or more amino acids added to, or removed from, either end of the disclosed peptides. Preferably, any added amino acids would be the same as the corresponding amino acids of a native retroviral protein. Such a longer or shorter peptide would be within the scope of the subject invention as long as said peptide is shorter than the full length retroviral protein and said longer or shorter peptide retains substantially the same relevant biological activity as the peptides exemplified herein. For example, a longer or shorter variant of the HIV-1 Nef(123–160) [SEQ ID NO. 18] peptide would fall within the scope of the subject invention if said variant had the ability to block the binding of SEA superantigen to class II MHC molecules. Also within the scope of the subject invention are peptides which have the same amino acid sequences of a peptide exemplified herein except for amino acid substitutions, additions, or deletions, as long as these variant peptides retain substantially the same relevant biological activity as the peptides specifically exemplified herein. For example, conservative amino acid substitutions within a peptide which do not affect the ability of the peptide to, for example, block the binding of SEA to class II MHC molecules would be within the scope of the subject invention. The peptides designated herein by the "viral peptide" designation, i.e., MMTV ORF(76–119), FIV ORF4(1–30), HIV-1 Nef(123–160), etc., should be understood to include variants and fragments, as discussed above, of the specifically exemplified sequences.

The subject invention further includes nucleotide sequences which encode the superantigen proteins and peptides disclosed herein. These nucleotide sequences could be readily constructed by those skilled in the art having the knowledge of the protein and peptide sequences which are presented herein. As would be appreciated by one skilled in the art, a variety of nucleotide sequences could be constructed to encode a particular peptide or protein due to the degeneracy of the genetic code. The choice of a particular nucleotide sequence could depend, for example, upon the codon usage of a particular expression system.

The Nef protein of the subject invention can be used to induce a lymphoproliferative response either in vitro or in vivo. The Nef protein can also be used to activate lymphocytes to produce clinically important cytokines such as IFNγ and IL-2. In addition, the Nef peptides of the subject invention can be used to modulate responses to superantigens. In a preferred embodiment, the Nef(123–160) [SEQ ID NO. 18] peptide can also be used to inhibit lymphocyte activation and cell proliferation induced by superantigens, including Nef and SEA. The Nef(123–160) [SEQ ID NO. 18] peptide can also be used to inhibit the production of cytokines and lymphokines that are induced by superantigens. Thus, the Nef protein and peptides of the subject invention can be used in treating clinically important conditions of animals and humans. Using the teachings described herein, the skilled artisan can use the subject invention to up regulate or down regulate immune responses.

As described herein, the peptide sequences of the subject invention can also be the basis for producing peptide antagonists. These antagonists are also within the scope of the subject invention. Inhibition or antagonism of retroviral superantigen function without agonist activity can be accomplished through the use of anti-peptide antibodies or modification of residues within the peptide itself. An especially productive means for generation of peptide antagonists has been substitution of L-amino acids with D-amino acids. The efficacy of this approach has been well characterized in the generation of arginine vasopressin analogs with selectively enhanced antidiuretic antagonism by appropriate substitution of L- with D-amino acids (Manning, M., W. H. Sawyer [1985] In: *Vasopressin*, Schrier, R. W., ed., Raven Press, New York, pp. 131–144). Further, not only can antagonism be produced with D-amino acid substitutions, but this antagonism can be directed toward a specific function. This targeting is desirable for superantigen antagonism because of the numerous superantigen activities. The binding affinity/avidity and specific activity of agonist and antagonist peptides can be further enhanced through chemical synthesis of multivalent forms of the agonist and/or antagonist peptides of superantigen activity. Production of potent antagonist peptides will be of value in specifically manipulating immune function and in protection from superantigen-induced disease.

A further aspect of the claimed invention is the use of the claimed peptides to produce antibodies. These antibodies can be produced using standard procedures well known to those skilled in the art. These antibodies may be used as diagnostic and therapeutic reagents. For example, antibodies that bind to the HIV-1 Nef protein may be used as an antagonist to inhibit the deleterious effects of the Nef protein. Antibodies that are reactive with the superantigen proteins of the subject invention can also be used to purify the protein from a crude mixture. The subject invention also includes antibodies that bind to class II MHC molecules and effectively prevent the binding of a retroviral superantigen, or a peptide fragment thereof, to class II MHC molecules. These antibodies can also be produced using procedures that are commonly employed by those skilled in the art.

The peptides are also useful as vaccines to prevent retroviral infections in non-infected individuals, and as immunotherapeutic reagents to help control retroviral pathogenesis in individuals already infected by a retrovirus. For example, to the extent that the HIV-1 Nef superantigen is required for infection and progress of the disease state, then antagonists of Nef activity can be used to help control the progression of AIDS, as well as to prevent infection.

In addition to their use in treating various disease states, the peptides can also be used to detect the presence of antibodies that are reactive with retroviral superantigen proteins in serum or other bodily fluid samples. For example, the Nef peptides can be used in standard ELISA and RIA assays to detect the presence of anti-Nef antibodies present in a sample. The superantigen proteins and peptides of the subject invention are also useful for stimulating peripheral mononuclear cells in vitro. This can be important, for example, in a variety of diagnostic procedures.

The teachings provided herein can be used by those skilled in the art to locate agonist and antagonist peptides from other retroviral superantigens.

Materials and Methods

Nef protein. Purified Nef protein was obtained from three sources. Nef protein obtained from Repligen (Cambridge, Mass.) was >95% pure and Nef protein obtained from the NIH AIDS Research and Reference Reagent Program (Rockville, Md.) was >90%. The Nef protein was also produced recombinantly in-house and purified to greater than 95% purity. Nef protein from all three sources had similar activity.

Reagents. Raji cells are EBV-transformed B cells that express DR3, Dw10, DQw1, and DQw2. L cells and mouse A20 cells were obtained from the American Type Culture Collection (ATCC) in Rockville, Md.

SEA was obtained from Toxin Technology (Sarasota, Fla.). Polymyxin B was obtained from Sigma Chemical Co. (St. Louis, Mo.). Purified recombinant Nef protein was obtained from Repligen Corporation (Cambridge, Mass.).

Synthetic peptides. Overlapping peptides corresponding to a region within the MMTV superantigen, amino acids 76–119, 117–147, 142–172, 166–195, 190–222, 220–250, 245–276, and 274–313 were synthesized. The amino acid sequence of the MMTV ORF was derived from Pullen, A. M., Y. Choi, E. Kushnir, J. Kappler, P. Marrack, [1992] *J. Exp. Med*. 175:41–47. In addition, a peptide with a scrambled sequence of amino acids 76–119 was synthesized. The MMTV ORF(76–119) [SEQ ID NO. 1] scrambled peptide sequence was generated using the sequence edit program of Devereax, J., P. Haeberli, O. Smithies [1984] *Nucleic Acids Res*. 12:387–395.

Overlapping peptides corresponding to the entire FIV ORF4 region, amino acids 1–30, 21–55, 31–65, and 51–71 were synthesized. The amino acid sequence of the FIV ORF4 peptides was obtained from Olmstead, R. A., V. M. Hirsch, R. H. Purcell, P. R. Johnson [1989] *Proc. Natl. Acad. Sci. USA* 86:8088–8092.

Overlapping peptides corresponding to the entire HIV-1 Nef protein, amino acids 1–38, 31–65, 62–99, 93–132, 123–160, 156–186, and 182–206 were synthesized. The amino acid sequence of the Nef peptides was based on the LAV strain of HIV-1 (this strain is also referred to as the HIVLAI strain in the Los Alamos Database) and was obtained from Wain–Hobson, S., P. Sonigo, O. Danos, S. Cole, M. Alizon [1985] *Cell* 40:9–17. Sequences of the Nef protein of other HIV-1 strains can be obtained from the Los Alamos Database on Human Retroviruses.

All peptides were synthesized using a Biosearch 9500AT automated peptide synthesizer using N-(9-flurenyl) methoxycarbonyl chemistry (Chang, C. D., J. Meienhofer [1978] *Int. J. Peptide Protein Res*. 11:246). Peptides were cleaved from the resins using trifluoroacetic acid/ethanedithiol/thioanisole/anisole at a ratio of 90/3/5/2. The cleaved peptides were then extracted in ether and ethyl acetate and subsequently dissolved in water and lyophilized. Peptides were extensively dialyzed against water to remove the remaining cleavage products. Reverse phase HPLC analysis of crude peptides indicated one major peak in each profile. Hence, further purification was not warranted. Amino acid analysis of these peptides showed that the amino acid composition corresponded closely to theoretical.

Radioiodinations. Staphylococcal enterotoxins and synthetic peptides were radioiodinated using chloramine T as described elsewhere (Torres, B. A., N. D. Griggs, H. M. Johnson [1993] Nature 364:152–154). Briefly, ligands were labeled with 500 µCi of Na$^{125}$I (15 mCi/µg, Amersham Corp., Arlington Heights, Ill.) in 25 µl of 0.5 M potassium phosphate buffer, pH 7.4, and 10 µl of chloramine T (5 mg/ml) for 2 minutes. After neutralization of the reaction with 10 µl volume each of sodium bisulfite (10 mg/ml), potassium iodide (70 mg/ml), and BSA (20 mg/ml), and 15 µl of NaCl (4 M), the preparation was sieved on a 5 ml Sepharose G-10 column. The two fractions with the highest radioactivity in the first eluted peak were pooled and used in the radiolabeled binding assays. The specific activities of the staphylococcal enterotoxins and synthetic peptides ranged from 70–120 µCi/µg and 30–40 µCi/µg, respectively.

Class II MHC binding studies. For binding studies using A20 cells, 1×10$^6$ A20 cells were incubated in 1.5 ml Eppendorf tubes with unlabeled competitors at room temperature for 45 minutes, followed by the addition of radiolabeled SEs or peptide. After an additional 45 minutes, one hundred microliters of reaction mixture was transferred to Ultrafree MC 5 µ filter units to which 300 microliters of binding buffer had been added. Filter units were centrifuged at 14,000 rpm for two minutes and the radioactivity remaining in the filter units was quantified using a gamma counter.

For I-A peptide binding studies, synthetic I-Aβ$^b$(60–90) peptide (in 200 µl of 25 µg/ml solution in 0.1M bicarbonate/carbonate buffer, pH 9.6) was absorbed to the bottoms of 12 mm by 55 mm polystyrene tubes for 6 hours at 4 degrees Centigrade. The tubes were washed three times and the remaining active sites were blocked with PBS containing 0.5%BSA (2 ml/tube) overnight at 4 degrees Centigrade. After three washes, competitors (100 µl in PBS/BSA) were added for 4 hours at room temperature, followed by the addition of 5 nM (final concentration) of either $^{125}$I-SEA or $^{125}$I-MMTV ORF(76–119) [SEQ ID NO. 1] peptide in 100 µl volumes. The tubes were washed three times and the bound radioactivity was quantified using an gamma counter.

For binding studies using Raji cells, unlabeled competitors (SEs and peptides) in a 50 µl volume of PBS containing 1% BSA were added to 50 µl of 1×10$^5$ Raji cells in Eppendorf tubes to reach the final indicated concentrations. Competitors were incubated with cells at room temperature for 45 minutes, followed by the addition of radiolabeled SEs or peptide. After 45 minutes, the cells were washed three times, pelleted and the bottoms of the tubes were cut off. Radioactivity in the bottom of the tube was quantified using a gamma counter.

Cell proliferation assay. Peripheral blood donated by healthy volunteers was used as a source of human peripheral mononuclear cells (PMNC). PMNC were isolated from blood using Histapaque (Sigma Chemical Co., St. Louis, Mo.) density centrifugation at 1600 rpm for 20 minutes. Isolated PMNC were washed three times with RPMI 1640 medium (J. R. Scientific, Woodland, Calif.) to remove residual Histapaque. After the final wash, PMNC were resuspended in RPMI 1640 containing 5% fetal bovine serum (Intergen, Purchase, N.Y.). 2×10$^5$ PMNC/well and the purified Nef protein were plated in triplicate into the wells of 96-well microtiter plates in a final volume of 0.15 ml/well. Cultures were incubated at 37 degrees Centigrade in 5% CO$_2$. Cultures were pulsed with $^3$H-thymidine ($^3$H-TdR; 1 µCi/well; Amersham Corp., Arlington Heights, Ill.) 18 hours prior to harvest at the 96 hour time point. Cells were harvested using a PHD cell harvester (Cambridge, Mass.), washed with distilled water, and $^3$H-thymidine incorporation was determined as counts per minute (CPM) in a β-scintillation counter. All experiments were performed in triplicate. The stimulation index was determined by using the following equation:

$$\text{Stimulation Index} = \frac{\text{EXPERIMENTAL CPM} - \text{CONTROL CPM}}{\text{CONTROL CPM}}$$

Inhibition of cell proliferation. Human PMNC were isolated as described in the cell proliferation assay above. 50 µl of cells at 2.8×10$^6$ cells/ml were added to the wells of a microtiter plate. Mitogens, superantigens and NeF peptides were added to the wells and cells were incubated at 37° C. for a total of 96 hours. $^3$H-thymidine (1 µCi/well) was added after 90 hours incubation and the cells incubated for an additional 6 hours prior to harvest onto filter paper as described above. Radioactivity was quantified using a liquid scintillation counter and the stimulation index calculated as shown above.

PMNC fractionation/reconstitution assay. T cells were isolated from PMNC using Cellect affinity columns (Biotex Corporation, Edmonton, Alberta, Canada). These columns trap B cells and monocytes, allowing T cells to pass through the column. This results in greater then 95% pure populations of T cells. T cells were counted and 50 µl of cells at 2.8×10$^6$ cells/ml were added to the wells of microtiter plates.

Antigen-presenting cells (APC) were generated in the following manner. PMNC from the same donor were treated with 0.8% paraformaldehyde for 10 minutes. Paraformaldehyde freezes the membranes of cells, allowing class II MHC antigens to interact with superantigens, but not allowing bound antigens to be internalized and processed. Cells were extensively washed and allowed to leach excess paraformaldehyde by incubating the cells at 37° C. for 1 hour. The paraformaldehyde treated APC are able to present superantigens but not specific antigens. Thus, use of paraformaldehyde treated APC can differentiate between superantigens and specific antigens. APC were counted and 50 µl of cells at 2.8×10$^6$ cell/ml were added to the wells of a microtiter plates.

Mitogens and superantigens were added and cells were incubated at 37° C. for a total of 96 hours. $^3$H-thymidine (1 µCi/well) was added at 90 hours and the cells were incubated for an additional 6 hours prior to harvest onto filter paper. Radioactivity was quantified using a liquid scintillation counter. Stimulation index (S.I.) was calculated as shown above.

IFN induction assay. PMNC (100 µl of 1×10$^7$ cells/ml) were cultured in the presence of SEA (100 ng/ml), Nef (100 ng/ml), and ConA (10 µg/ml) in the wells of 24-well plates in a final volume of 300 µl of culture media. 100 µl samples were removed at 24, 48, 72, and 96 hours after initiation of cultures. IFN was assayed by a microplaque reduction method, using approximately 40 PFU of vesicular stomatitis virus (VSV) per well on human WISH cells. 1 U/ml of IFN is defined as the concentration required to decrease the number of PFU per well by 50%.

The IFN activity induced was IFNγ, as determined by neutralization reactions with specific antisera. Samples from SEA and Nef treated cell cultures were pretreated with 1000 neutralizing units of anti-IFNα or anti-IFNγ. Controls were sham-treated with media alone. Samples were incubated at 37° C. for 1 hour prior to transfer to human WISH cells. Residual IFN activity was measured as described above.

Following are examples which illustrate procedures, including the best mode, for practicing the invention. These examples should not be construed as limiting. All percentages are by weight and all solvent mixture proportions are by volume unless otherwise noted.

EXAMPLE 1

Dose-Response Binding of MMTV ORF Peptides to Cells Expressing Class II MHC Molecules The dose-response binding of MMTV ORF peptides to a cell line expressing class II MHC molecules on its surface was assessed in a competitive inhibition protocol using $^{125}$I-SEA. MMTV ORF(76–119) [SEQ ID NO. 1] peptide reduced $^{125}$I-SEA binding to A20 cells by 50% at a concentration of 20 μM. Unlabeled SEA was 20 times more effective a competitor than MMTV ORF(76–119) [SEQ ID NO. 1], which is consistent with the reported $K_d$ value for SEA binding to I-$E^d$. Therefore, MMTV ORF(76–119) [SEQ ID NO. 1] peptide competes with SEA for binding to A20 cells in a dose-dependent manner.

EXAMPLE 2

Binding of MMTV ORF(76–119) [SEQ ID NO. 1] Peptide to Class II MHC β-Chain Peptide The direct binding of $^{125}$I-SEA and MMTV $^{125}$I-MMTV ORF(76–119) [SEQ ID NO. 1] peptide to I-A$β^b$(60–90) peptide was assessed by competitive radioimmunoassay. It was previously shown that SEA binds to the α-helical region of the class II MHC β-chain outside the antigen binding groove (Russel, J. K, C. H. Pontzer, H. M. Johnson [1991] *Proc. Natl. Acad. Sci. USA* 88:7228–7232). This region is encompassed by amino acid residues 60–90 of the β-chain. SEA and MMTV ORF(76–119) [SEQ ID NO. 1] both competed with $^{125}$I-SEA and $^{125}$I-MMTV ORF(76–119) [SEQ ID NO. 1] for binding to I-A$β^b$(60–90) peptide in a manner similar to the competition seen on whole cells. These results are consistent with the peptide binding data indicating class II MHC as the binding site of MMTV ORF(76–119) [SEQ ID NO. 1], and suggest that SEA and MMTV ORF(76–119) [SEQ ID NO. 1] bind to a similar region on the β-chain of the class II MHC molecule.

EXAMPLE 3

Detection of FIV ORF4 Peptides by Antibodies from FIV-vaccinated and FIV-Infected Cats Antisera from FIV-vaccinated and FIV-infected cats was assessed for the presence of antibodies reactive with the ORF4 peptides through an ELISA immunoassay. Viral-neutralizng serum obtained from virus-vaccinated and cell-vaccinated cats was reactive with FIV ORF4(1–30) [SEQ ID NO. 10] and FIV ORF4(21–55) [SEQ ID NO. 11] peptides. However, antisera reactivity was greatest with the FIV ORF4(1–30) [SEQ ID NO. 10] peptide. Pooled antisera drawn at various time intervals from FIV-infected cats reacted with all four of the ORF4 peptides. The peak reactivity was observed at 10 weeks post-infection, although all of the peptides except FIV ORF4(1–30) [SEQ ID NO. 10] showed a second peak of reactivity at about 220 weeks post-infection. This data suggests that the FIV superantigen protein corresponding to the ORF4 peptide fragments is expressed in vivo, since antisera from FIV-vaccinated and FIV-infected cats both react with the ORF4 peptides.

Figure 2:
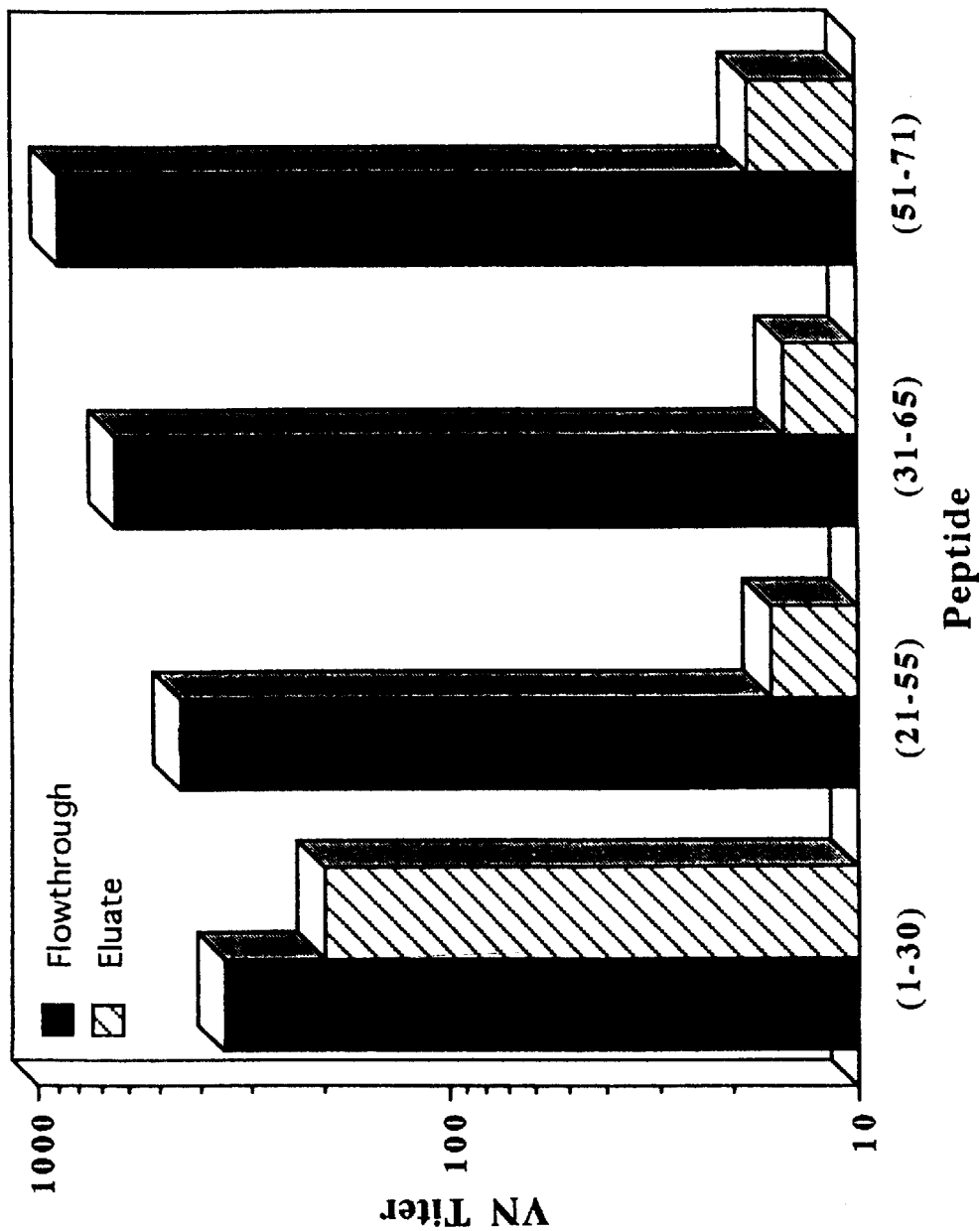
FIG. 2. FIV neutralization by anti-peptide reactive antibodies purified using FIV ORF4 peptide immunoaffinity columns. The viral neutralizing (VN) titer of antibodies isolated from pooled sera of FIV-vaccinated cats is shown for the flow-through and the eluate of each FIV peptide immunoaffinity column.

Immunoaffinity columns were prepared for each of the four ORF4 peptides using standard procedures. Partially purified antisera pooled from virus-vaccinated cats, which had previously been shown to protect cats from infection in passive immunization studies, was passed through an ORF4 peptide immunoaffinity column in order to purify any of the antibodies in the antisera that reacted with the particular peptide. Both the flow-through and the eluate from each column were tested for activity in a viral neutralization assay. High viral neutralization activity was observed in the eluate fraction from the FIV ORF4(1–30) [SEQ ID NO. 10] peptide column (FIG. 2). Fractions eluted from the other peptide columns did not contain viral neutralization activity, all of the viral neutralization activity being detected in the flow-through fraction of these columns.

This demonstrates a strong correlation between the presence of serum neutralizing antibodies and antibodies that are reactive with FIV ORF4 peptides. The viral neutralizing antibodies present in virus-vaccinated cats apparently recognize the N-terminal portion of the FIV ORF4(1–30) [SEQ ID NO. 10], since a 9 amino acid overlap occurs between FIV ORF4(1–30) [SEQ ID NO. 10] and FIV ORF4(21–55) [SEQ ID NO. 11].

EXAMPLE 4

Proliferative Response of Human Peripheral Mononuclear Cells to Recombinant HIV-1 Nef Protein Nef protein was tested for its effect on proliferation of human peripheral mononuclear cells. The results of a representative experiment are shown in FIG. 4. Cell proliferation responses to Nef protein varied between individuals, but significant proliferation could consistently be seen after 48 and 96 hours stimulation with 0.3–3 μg/ml of Nef.

EXAMPLE 5

Dose-Response Binding of HIV-1 Nef(123–160) [SEQ ID NO. 18] Peptide to Cells Expressing Human Class II MHC Molecules The dose-response binding of HIV-1 Nef peptides to a human cell line expressing class II MHC molecules was assessed using a competitive inhibition protocol. HIV-1 Nef(123–160) [SEQ ID NO. 18] peptide reduced the binding of $^{125}$I-SEA to Raji cells by approximately 20% at a concentration of 30 μM, and approximately 40% at a concentration of 300 μM. HIV-1 Nef(1–38) [SEQ ID NO. 14] and HIV-1 Nef(31–65) [SEQ ID NO. 15] slightly reduced the binding of $^{125}$I-SEA to Raji cells at a peptide concentration of 300 μM.

EXAMPLE 6

Vaccines

The novel superantigen proteins and peptides described herein can be used advantageously in an immunogenic composition such as a vaccine. Such a composition, when administered to a person or animal, raises antibodies or other immune responses which reduce the susceptibility of that human or animal to infection by a virus expressing that superantigen.

Vaccines comprising the superantigen proteins and peptides disclosed herein, and variants thereof having antigenic or immunogenic properties, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminum hydroxide or muramyl dipeptide or variations thereof. Also, cholera toxin subunit B or other agents which stimulate antibody production at mucosal sites can be used. In the case of peptides, coupling to larger molecules such as KLH or tetanus toxoid sometimes enhances immunogenicity. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

The compounds can be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered can depend on the subject to be treated and the degree of protection desired. Precise amounts of active ingredient required to be administered depend on the judgment of the practitioner and can be peculiar to each individual. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for stimulating an immune response in an animal, said method comprising administering to said animal an effective amount of an immunogenic composition comprising a retroviral superantigen peptide, wherein said superantigen peptide is a peptide selected from the group consisting of a peptide designated HIV-1 Nef(1–38) consisting of an amino acid sequence shown in SEQ ID NO. 14 and a peptide designated HIV-1 Nef(123–160) consisting of an amino acid sequence shown in SEQ ID NO. 18, wherein said immune response is selected from the group consisting of antibody production by B lymphocytes, proliferation of $CD4^+$ lymphoctes, the production of IL-2, and the production of IFN-γ.

2. An immunogenic composition wherein said immunogenic composition comprises a retroviral superantigen peptide, wherein said superantigen peptide is a peptide selected from the group consisting of a peptide designated HIV-1 Nef(1–38) consisting of an amino acid sequence shown in SEQ ID NO. 14 and a peptide designated HIV-1 Nef (123–160) consisting of an amino acid sequence shown in SEQ ID NO. 18, in a pharmacologically-acceptable vehicle.

3. The method according to claim 1, wherein said immune response is antibody production by B lymphocytes.

4. The method according to claim 1, wherein said immune response is proliferation of $CD4^+$ lymphocytes.

5. The method according to claim 1, wherein said immune response is production of IL-2.

6. The method according to claim 1, wherein said immune response is production of IFN-γ.

* * * * *

UNITED STATES PATENT AND TRADEMARK OFFICE
CERTIFICATE OF CORRECTION

PATENT NO. : 5,968,514

DATED : October 19, 1999

INVENTOR(S) : Howard M. Johnson, Barbara A. Torres, Janet K. Yamamoto

It is certified that error appears in the above-identified patent and that said Letters Patent is hereby corrected as shown below:

Column 2, line 3: "cytolines" should read --cytokines--.

Column 2, line 48: "Vβ" should read --$V_\beta$--.

Column 3, line 1: "enterotoxdns" should read --enterotoxins--.

Column 3, line 47: "et aL.," should read --*et al.*,--.

Column 6, lines 31 and 39: "NeF" should read --Nef--.

Column 10, line 65: "NeF" should read --Nef--.

Column 11, line 3: "NeF" should read --Nef--.

Column 12, line 7: "II)" should read --ID--.

Signed and Sealed this

First Day of August, 2000

Attest:

Attesting Officer

Q. TODD DICKINSON
Director of Patents and Trademarks

```
SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
         (A) LENGTH: 44 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Asp Ser Phe Asn Asn Ser Ser Val Gln Asp Tyr Asn Leu Asn Asp Ser
1               5                   10                  15

Glu Asn Ser Thr Phe Leu Leu Gly Gln Gly Pro Gln Pro Thr Ser Ser
            20                  25                  30

Tyr Lys Pro His Arg Leu Cys Pro Ser Glu Ile Glu
        35                  40

(2) INFORMATION FOR SEQ ID NO:2:

(i) SEQUENCE CHARACTERISTICS:
         (A) LENGTH: 31 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:
```

```
Glu Ile Glu Ile Arg Met Leu Ala Lys Asn Tyr Ile Phe Thr Asn Glu
1               5                   10                  15

Thr Asn Pro Ile Gly Arg Leu Leu Ile Met Met Leu Arg Asn Glu
            20                  25                  30
```

(2) INFORMATION FOR SEQ ID NO:3:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Met Leu Arg Asn Glu Ser Leu Ser Phe Ser Thr Ile Phe Thr Gln
1               5                   10                  15

Ile Gln Arg Leu Glu Met Gly Ile Glu Asn Arg Lys Arg Ser
            20                  25                  30
```

(2) INFORMATION FOR SEQ ID NO:4:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Glu Asn Arg Lys Arg Arg Ser Thr Ser Val Glu Glu Gln Val Gln Gly
1               5                   10                  15

Leu Arg Ala Ser Gly Leu Glu Val Lys Arg Gly Lys Arg Ser
            20                  25                  30
```

(2) INFORMATION FOR SEQ ID NO:5:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Lys Arg Gly Lys Arg Ser Ala Leu Val Lys Ile Gly Asp Arg Trp Trp
1               5                   10                  15

Gln Pro Gly Thr Tyr Arg Gly Pro Tyr Ile Tyr Arg Pro Thr Asp Ala
            20                  25                  30
Pro
```

(2) INFORMATION FOR SEQ ID NO:6:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Asp Ala Pro Leu Pro Tyr Thr Gly Arg Tyr Asp Leu Asn Phe Asp Arg
1               5                   10                  15
```

Trp Val Thr Val Asn Gly Tyr Lys Val Leu Tyr Arg Ser Leu Pro
            20                  25                  30

(2) INFORMATION FOR SEQ ID NO:7:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Leu Tyr Arg Ser Leu Pro Phe Arg Glu Arg Leu Ala Arg Ala Arg Pro
1               5                   10                  15

Pro Trp Cys Val Leu Ser Gln Glu Glu Lys Asp Asp Met Lys Gln Gln
            20                  25                  30

(2) INFORMATION FOR SEQ ID NO:8:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Lys Gln Gln Val His Asp Tyr Ile Tyr Leu Gly Thr Gly Met Ile His
1               5                   10                  15

Trp Lys Val Phe Tyr Asn Ser Arg Glu Glu Ala Lys Arg His Ile Ile
            20                  25                  30

Glu His Ile Lys Ala Leu Pro
            35

(2) INFORMATION FOR SEQ ID NO:9:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Pro Asn Ser Asn Glu Gly Leu Ser Gln Gln Ser Thr Asp Pro Ser Pro
1               5                   10                  15

His Asn Phe Ile Leu Ser Asn Glu Asn Ser Tyr Pro Cys Tyr Ser Leu
            20                  25                  30

Leu Gly Asp Val Gln Arg Glu Asp Ser Thr Lys Phe
            35                  40

(2) INFORMATION FOR SEQ ID NO:10:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Gly Lys Arg Lys Arg Gln Arg Arg Arg Lys Lys Lys Ala Phe Lys
1               5                   10                  15

Arg Met Met Thr Glu Leu Glu Asp Arg Phe Arg Lys Leu Phe
                20                  25                  30
```

(2) INFORMATION FOR SEQ ID NO:11:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Glu Leu Glu Asp Arg Phe Arg Lys Leu Phe Gly Thr Thr Ser Thr Thr
1               5                   10                  15

Gly Asp Ser Thr Val Asp Ser Glu Asp Glu Pro Pro Lys Lys Glu Lys
                20                  25                  30

Arg Val Asp
        35
```

(2) INFORMATION FOR SEQ ID NO:12:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Gly Thr Thr Ser Thr Thr Gly Asp Ser Thr Val Asp Ser Glu Asp Glu
1               5                   10                  15

Pro Pro Lys Lys Glu Lys Arg Val Asp Trp Asp Glu Tyr Trp Asn Pro
                20                  25                  30

Glu Glu Ile
        35
```

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Glu Lys Arg Val Asp Trp Asp Glu Tyr Trp Asn Pro Glu Glu Ile Glu
1               5                   10                  15

Arg Met Leu Met
        20
```

(2) INFORMATION FOR SEQ ID NO:14:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Met Gly Gly Lys Trp Ser Lys Ser Ser Val Val Gly Trp Pro Thr Val
1               5                   10                  15

Arg Glu Arg Met Arg Arg Ala Glu Pro Ala Ala Asp Gly Val Gly Ala
                20                  25                  30

Ala Ser Arg Asp Leu Glu
            35

(2) INFORMATION FOR SEQ ID NO:15:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gly Ala Ala Ser Arg Asp Leu Glu Lys His Gly Ala Ile Thr Ser Ser
1               5                   10                  15

Asn Thr Ala Ala Thr Asn Ala Ala Cys Ala Trp Leu Glu Ala Gln Glu
                20                  25                  30

Glu Glu Glu
        35

(2) INFORMATION FOR SEQ ID NO:16:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Glu Glu Glu Glu Val Gly Phe Pro Val Thr Pro Gln Val Pro Leu Arg
1               5                   10                  15

Pro Met Thr Tyr Lys Ala Ala Val Asp Leu Ser His Phe Leu Lys Glu
                20                  25                  30

Lys Gly Gly Leu Glu Gly
            35

(2) INFORMATION FOR SEQ ID NO:17:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Glu Lys Gly Gly Leu Glu Gly Leu Ile His Ser Gln Arg Arg Gln Asp
1               5                   10                  15

Ile Leu Asp Leu Trp Ile Tyr His Thr Gln Gly Tyr Phe Pro Asp Trp
                20                  25                  30

Gln Asn Tyr Thr Pro Gly Pro Gly
            35                  40

(2) INFORMATION FOR SEQ ID NO:18:

```
        (i) SEQUENCE CHARACTERISTICS:
            (A) LENGTH: 38 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Asp Trp Gln Asn Tyr Thr Pro Gly Pro Gly Val Arg Tyr Pro Leu Thr
1               5                   10                  15

Phe Gly Trp Cys Tyr Lys Leu Val Pro Val Glu Pro Asp Lys Val Glu
                20                  25                  30

Glu Ala Asn Lys Gly Glu
            35

(2) INFORMATION FOR SEQ ID NO:19:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:19:

Asn Lys Gly Glu Asn Thr Ser Leu Leu His Pro Val Ser Leu His Gly
1               5                   10                  15

Met Asp Asp Pro Glu Arg Glu Val Leu Glu Trp Arg Phe Asp
                20                  25                  30

(2) INFORMATION FOR SEQ ID NO:20:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:20:

Glu Gln Arg Phe Asp Ser Arg Leu Ala Phe His His Val Ala Arg Glu
1               5                   10                  15

Leu His Pro Glu Tyr Phe Lys Asn Cys
                20                  25
```